(12) United States Patent
Ren et al.

(10) Patent No.: US 9,597,009 B2
(45) Date of Patent: Mar. 21, 2017

(54) MARKER-BASED TOOL TRACKING (71) Applicant: Novartis AG, Basel (CH)

(72) Inventors: Hugang Ren, Irvine, CA (US);
Lingfeng Yu, Rancho Santa Margarita, CA (US)

(73) Assignee: Novartis AG, Basel (CH)

( * ) Notice: Subject to any disclaimer, the term of this patent is extended or adjusted under 35 U.S.C. 154(b) by 445 days.

(21) Appl. No.: 14/134,237

(22) Filed: Dec. 19, 2013

(65) Prior Publication Data

US 2015/0173644 A1 Jun. 25, 2015

(51) Int. Cl.
| | |
|---|---|
| *A61B 5/05* | (2006.01) |
| *A61B 5/06* | (2006.01) |
| *A61B 5/00* | (2006.01) |
| *A61B 3/10* | (2006.01) |
| *A61B 3/13* | (2006.01) |

(Continued)

(52) U.S. Cl.
CPC ............. *A61B 5/066* (2013.01); *A61B 3/102* (2013.01); *A61B 3/13* (2013.01); *A61B 5/0059* (2013.01); *A61B 5/064* (2013.01); *A61B 5/6821* (2013.01); *A61B 34/25* (2016.02); *A61B 90/37* (2016.02); *A61F 9/00736* (2013.01); *A61B 2034/2065* (2016.02); *A61B 2090/365* (2016.02); *A61B 2090/368* (2016.02); *G02B 21/0012* (2013.01)

(58) Field of Classification Search
CPC ....... A61B 5/066; A61B 5/0073; A61B 3/145; A61B 5/055; A61B 5/064; A61B 5/0059; A61B 5/6821
See application file for complete search history.

(56) References Cited

U.S. PATENT DOCUMENTS

| | | | |
|---|---|---|---|
| 2003/0169603 A1 | 9/2003 | Luloh et al. | |
| 2009/0182312 A1* | 7/2009 | Gertner | A61F 9/008 606/4 |

(Continued)

FOREIGN PATENT DOCUMENTS

| | | |
|---|---|---|
| DE | 102004049258 A1 | 4/2006 |
| WO | WO 2005/107845 | 11/2005 |

(Continued)

OTHER PUBLICATIONS

International Search Report and Written Opinion issued for PCT/US2014/068899, dated Mar. 5, 2015, 8 pgs.

(Continued)

*Primary Examiner* — Joel Lamprecht (57) ABSTRACT

An ophthalmic surgical tool has a marker positioned at a distal portion of the ophthalmic surgical tool. The distal portion of the ophthalmic surgical tool is inserted into an eye along with the marker to perform surgeries in the eye. An imaging device captures images of the fundus of the eye including the distal portion of the ophthalmic surgical tool. An image processor processes the captured images to identify and extract the marker from the captured images. The marker has a high-contrast feature in a visible light or infrared light range or other spectral ranges. Thus, the image processor may identify and extract the marker from the captured images. Indicators may be generated based on the marker and be overlaid with the captured or processed images of the fundus and displayed to a user to indicate surgical information to the user.

20 Claims, 4 Drawing Sheets

(51) Int. Cl.
*A61F 9/007* (2006.01)
*A61B 34/00* (2016.01)
*A61B 90/00* (2016.01)
*G02B 21/00* (2006.01)
*A61B 34/20* (2016.01)

(56) References Cited

U.S. PATENT DOCUMENTS

| | | |
|---|---|---|
| 2010/0168763 A1* | 7/2010 | Zhao ................. A61B 34/30 606/130 |
| 2010/0208202 A1 | 8/2010 | Itoh et al. |
| 2011/0282331 A1 | 11/2011 | Brennan et al. |
| 2012/0071891 A1 | 3/2012 | Itkowitz et al. |
| 2013/0038836 A1 | 2/2013 | Smith |
| 2014/0005484 A1 | 1/2014 | Charles |
| 2015/0173644 A1 | 6/2015 | Ren et al. |

FOREIGN PATENT DOCUMENTS

| | | |
|---|---|---|
| WO | WO 2011/085815 A1 | 7/2011 |
| WO | WO 2014/170236 A1 | 10/2014 |

OTHER PUBLICATIONS

Sznitman et al., Unified Detection and Tracking in Retinal Microsurgery, MICCAI 2011, Part I, LNCS 6891, pp. 1-8 (2011).
Richa et al., Vision-Based Proximity Detection in Retinal Surgery, IEEE Transactions on Biomedical Engineering, vol. 59, No. 8, Aug. 2012, pp. 1-11.
Sznitman et al., Data-Driven Visual Tracking in Retinal Microsurgery, MICCAI 2012, Part II, LNCS 7511, pp. 568-575 (2012).-8.

* cited by examiner

MARKER-BASED TOOL TRACKING

BACKGROUND

The devices, systems, and methods disclosed herein relate generally to marker-based tool tracking, and more particularly, to devices, systems, and methods that are configured to perform marker-based tool tracking in ophthalmic surgeries.

Surgical tools, such as surgical imaging probes, surgical forceps, surgical scissors, surgical vitrectomy probes, and the like, may be inserted into an eye during an ophthalmic surgery to perform various surgeries in the eye. Typically, a distal portion of a surgical tool is inserted into the eye during the ophthalmic surgery. Thus, the area of the eye surrounding the distal tip of the surgical tool is a region of interest to a surgeon. To achieve guided surgical interventions, such as intra-operative Optical Coherence Tomography (OCT) for Internal Limited Membrane (ILM) peeling, automatic tool tip tracking is used to efficiently close a feedback loop to allow the OCT engine to locate the scanning target area. Further, to provide real time feedback during surgery, useful surgical data may be overlaid to the surgeon's current area of interest. When a surgeon moves the distal portion of the surgical tool inserted into the eye, the area of interest may shift accordingly. Thus, automatic tool tracking may be used to locate the area of interest to adjust the surgical data overlay so the surgeon may visualize it without looking away from the current area of interest.

There are three conventional techniques for general object tracking. The first technique is motion-based object tracking. Motion-based object tracking may be used for automated surveillance. Motion-based object tracking may use image processing algorithms, such as background subtraction, frame difference, and optical flow, to track an object. Nevertheless, motion-based object tracking algorithm requires a quasi-stationary background and may not be suitable for tool tracking in an ophthalmic surgery in which background may vary constantly.

The second technique for general object tracking is region-based object tracking. Region-based object tracking may be used for tracking simple objects. In region-based object tracking, an object template is preselected offline or during a first frame. For the subsequent frames, the template is searched across the whole field of view and the location with the greatest similarity to the template is identified as the object. Nevertheless, region-based object tracking is sensitive to object pose variations and local illumination changes and may not be suitable for tool tracking in an ophthalmic surgery, in which illumination and orientation of the tool vary greatly.

The third technique for general object tracking is feature-based object tracking. Feature-based object tracking may extract and search for unique features of an object, such as contour, edge, shape, color, corner/interest point and the like, across the entire field of view for object detection. Nevertheless, in the feature-based tracking algorithm, a high contrast feature, which is not sensitive to environmental and object pose changes and is unique to the object, is required. Since most of the surgical tools do not possess high contrast intrinsic features, feature based object tracking may not provide suitable results.

In a vitreo-retinal surgery, illumination conditions may be challenging for tool tracking. An endo illuminator may be inserted into the eye for illumination. Because the endo illuminator may move during a surgery, the illumination condition may vary greatly from image frame to image frame and the images of the fundus area being illuminated may change greatly over time. Motion-based and region-based object tracking techniques may be difficult to implement under inconsistent illumination conditions. Further, with a single illuminator illuminating from one side, shadow artifacts and specular reflection from the surgical tool may increase complexity for tool tracking. Moreover, in order to capture a fundus image through a video camera, a beam path of an imaging light from the eye may pass through multiple optical elements and media, such as eye vitreous body, an aged crystalline lens, eye cornea, and Binocular Indirect Ophthalmomicroscope (BIOM) lenses. These optical elements in the beam path of imaging light may further degrade the image quality and reduce contrast. Thus, it may be difficult to extract an intrinsic feature of various surgical tools to achieve real time tool tracking.

The present disclosure is directed to devices, systems, and methods that address one or more of the disadvantages of the prior art.

SUMMARY

In an exemplary aspect, the present disclosure is directed to an ophthalmic surgical tool tracking system. The ophthalmic surgical tool tracking system may include an ophthalmic surgical tool with a distal portion configured to be inserted into an eye, a marker positioned at the distal portion of the ophthalmic surgical tool, and a tool position detection system configured to determine a position of the distal portion of the ophthalmic surgical tool in the eye by detecting the marker.

The tool position detection system may include a light source configured to introduce light into the eye; an imaging device configured to capture an image of the eye along with the distal portion of the ophthalmic surgical tool inserted into the eye, a processor, and a display. The processor is configured to process the captured image to identify the marker, generate indicators indicating surgical data, such as a position of a surgical tool, an orientation of a surgical tool, an image, a surgical setting parameter, overlay the indicators on the captured image or a processed image. The display is configured to display the captured image or a processed image with the overlaid indicators. In another exemplary aspect, the present disclosure is directed to a method for tracking an ophthalmic surgical tool inserted into an eye. The method may include introducing an imaging light into an eye, capturing an image of the eye along with a distal portion of an ophthalmic surgical tool inserted into the eye, and determining a position of the distal portion of the ophthalmic surgical tool in the eye by detecting a marker positioned at the distal portion of the ophthalmic surgical tool.

In some aspects, determining a position of the distal portion may include processing the captured image to identify the marker, generating indicators indicating surgical data, such as a position of a surgical tool, an orientation of a surgical tool, an image, a surgical setting parameter, overlaying the indicators on the captured images or a processed image, and displaying the captured image or a processed image with the overlaid indicators on a display.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein provide an ophthalmic surgical tool tracking system that includes an ophthalmic surgical tool with a marker positioned at a distal portion of the ophthalmic surgical tool. The system tracks the location of the marker when the distal portion of the ophthalmic surgical tool, along with the marker, is inserted into an eye to perform surgeries in the eye. A light source, e.g., an endo illuminator, may introduce light into a fundus of the eye. The light may be reflected off the fundus of the eye and the distal portion of the ophthalmic surgical tool. An imaging device of the system may receive the reflected light to capture images of the fundus of the eye and the distal portion of the ophthalmic surgical tool.

The system also may include an image processor which may process the captured images to identify and extract the marker from the captured images. The marker may have a high-contrast feature in a visible light or infrared light range or other spectral ranges. Thus, the image processor may identify and extract the marker from the captured images. The location of the marker may be used to generate indicators indicating surgical data, such as a position of a surgical tool, an orientation of a surgical tool, an image, a surgical setting parameter. The indicators are then overlaid with the captured images of the fundus or processed images and displayed to a user. By using the above marker-based ophthalmic surgical tool tracking system, robust tool tracking may be implemented during the ophthalmic surgery, because the high-contrast marker is less sensitive to illumination changes or shadow artifacts that frequently occur in ophthalmic surgeries. Further, the system may indicate surgical data, such as a presence, position, and orientation of the surgical tool, an image, a surgical setting parameter in real time to assist a surgeon during an ophthalmic surgical operation in the eye.

Figure 1:
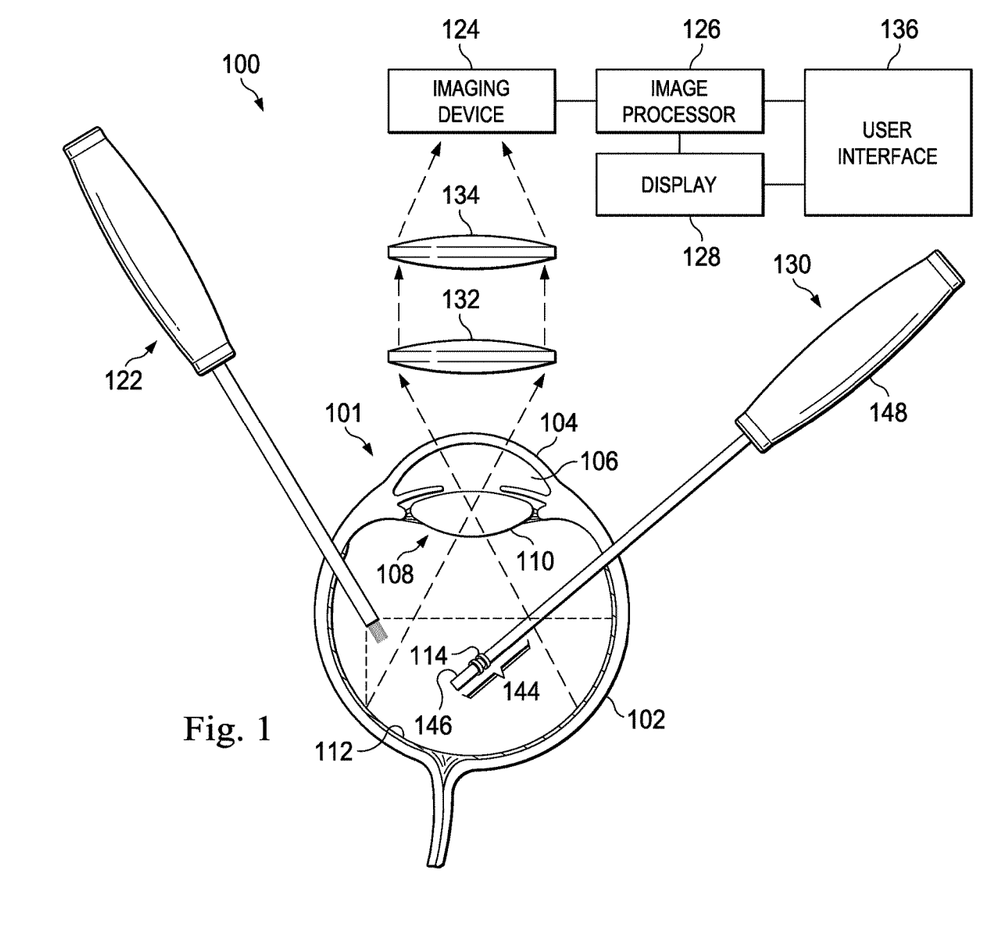
FIG. 1 illustrates a schematic diagram of an exemplary ophthalmic surgical tool tracking system according to an aspect consistent with the principles of the present disclosure.

FIG. 1 illustrates an exemplary ophthalmic surgical tool tracking system, generally designated 100 disposed relative to an eye 101 under treatment. The eye 101 includes sclera 102, a cornea 104, an anterior chamber 106, and a posterior chamber 108. A capsular bag 110 is illustrated in the posterior chamber 108. The eye 101 further includes a retina 112. An ophthalmic surgical tool 130 may be used to perform surgery in the eye 101. The ophthalmic surgical tool 130 may be sized and shaped to be handled by a surgeon and to protrude into the eye 101 of the patient.

The ophthalmic surgical tool 130 may include a proximal portion 148 and a distal portion 144. The proximal portion 148 may be sized and shaped for handheld grasping by a user. For example, the proximal portion 148 may define a handle which is sized and shaped for grasping by a single hand of the user. In use, the user may control the position of the distal portion 144 by maneuvering the proximal portion 148. The distal portion 144 of the ophthalmic surgical tool 130 may include a marker 114. The marker may have a high contrast feature in the visible light or infrared spectrum or other spectral ranges detectable by an imaging device 124 of the ophthalmic surgical tool tracking system 100.

The ophthalmic surgical tool tracking system 100 also may include a light source 122, e.g., an endo illuminator. The light source 122 may have a distal portion that is configured to be inserted into the eye 101. A distal tip of the light source 122 may emit an imaging light that may illuminate a fundus of the eye 101. The fundus is an interior surface of the eye 101 and may include the retina 112. The imaging light from the light source 122 may be reflected from the fundus and the distal portion 144 of the ophthalmic surgical tool 130. The reflected imaging light may pass through the capsular bag 110, the anterior chamber 106, the cornea 104, and be received by the imaging device 124, which is configured to capture fundus images of the eye 101. Lenses 132 and 134 may be provided between the eye 101 and the imaging device 124 to receive the reflected imaging light from the fundus and direct the imaging light to the imaging device 124.

In some embodiments, the imaging device 124 may include one or more video cameras configured to capture images of the fundus. The video camera may capture images in visible light spectrum, infrared spectrum or other spectral ranges. For example, imaging device 124 may include either or both a video camera that captures images of the fundus in visible light spectrum and a video camera that captures infrared images of an infrared marker 114 near the fundus in the infrared spectrum.

The ophthalmic surgical tool tracking system 100 also may include an image processor 126. The image processor 126 may receive image frames captured by the imaging device 124 and perform various image processing on the image frames. In particular, the image processor 126 may perform image analysis on the image frames to identify and extract the image of the marker 114 from the image frames. Further, the image processor 126 may generate indicators and overlay the indicators on the image of the fundus or a processed image. The indicators may include surgical data, such as the position and orientation of the marker 114 in the image of the fundus, the position and orientation of a distal tip 146 of the ophthalmic surgical tool 130, an image, a surgical setting parameter. The overlaid image may then be displayed by a display 128 to the user.

The imaging device 124, the image processor 126, and the display 128 may be implemented in separate housings communicatively coupled to one another or within a common console or housing. A user interface 136 may be associated with the display 128 and/or the image processor 126. It may include, for example, a keyboard, a mouse, a joystick, a touchscreen, an eye tracking device, a speech recognition device, a gesture control module, dials, and/or buttons, among other input devices. A user may enter desired instructions or parameters at the user interface 136 to control the imaging device 124 for taking images of the eye 101. During an ophthalmic surgery, a surgeon may review the images of the fundus and/or the overlaid indicators on the display 128 to visualize the operation and the relative position of the distal tip 146 of the ophthalmic surgical tool 130 within various portions of the fundus.

Figure 2:
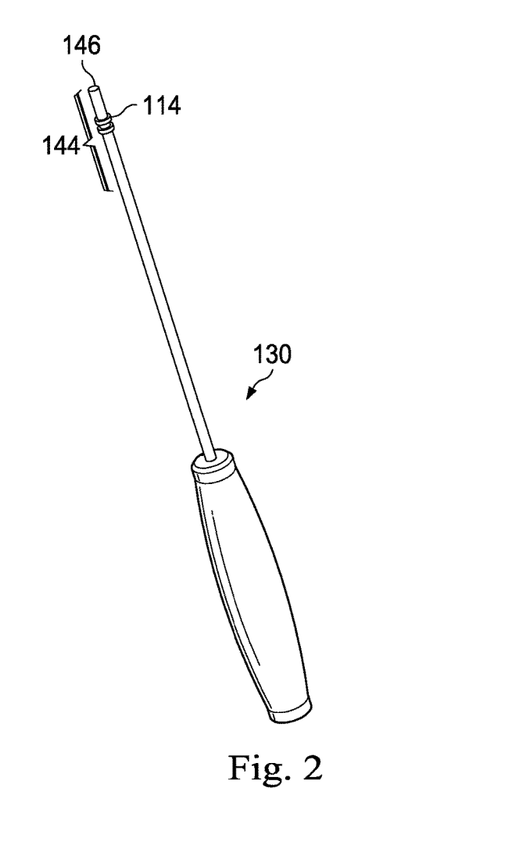
FIG. 2 illustrates a distal portion of an exemplary surgical tool according to an aspect consistent with the principles of the present disclosure.

FIG. 2 is an enlarged view of the distal portion 144 of the ophthalmic surgical tool 130. One or more markers 114 may be positioned at the distal portion 144. In particular, the markers 114 may wrap around the distal portion of the ophthalmic surgical tool 130, such that markers 114 may be visible in all directions even when the ophthalmic surgical tool 130 is rotated. The markers 114 may be labels or printed decals bonded to the ophthalmic surgical tool 130. The markers 114 may be formed with synthetic material, such as plastic. Thus, the markers 114 may not deteriorate in a biological tissue. Further, the markers 114 may be bio-compatible and do not interfere or react with biological tissues. In some embodiments, the markers 114 may be inscribed on an exterior surface of the ophthalmic surgical tool 130. Thus, the markers 114 may be a layer of paint inscribed on the exterior surface of the ophthalmic surgical tool 130. In some embodiments, the markers 114 may be embedded into the wall of the ophthalmic surgical tool 130. In addition, the markers 114 may have a high-contrast feature in visible, infrared or other spectrum. A high-contrast feature may be a color or a pattern that is distinguishable from colors or patterns in the fundus. For example, a high-contrast color may be a green color, which typically does not appear in a fundus of an eye. It is noteworthy that adding markers 114 should not increase the size of the surgical tools.

Figure 3:
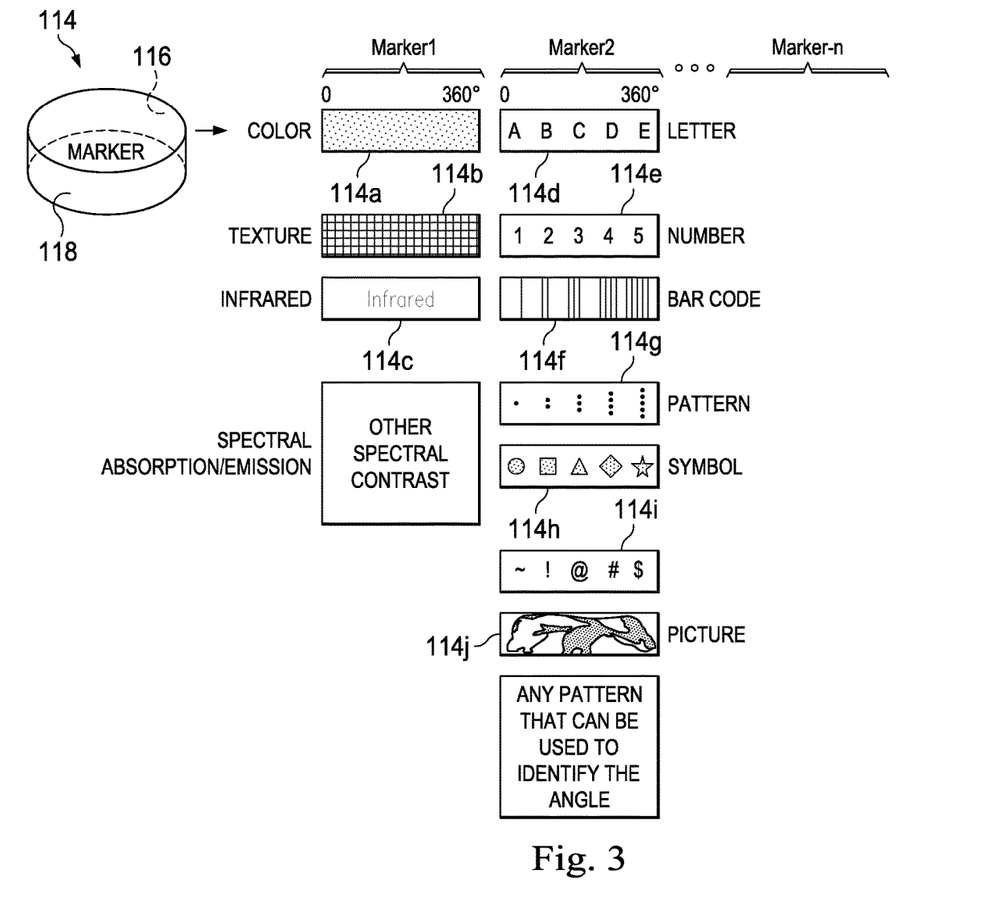
FIG. 3 illustrates a perspective view of a marker and various types of markers according to an aspect consistent with the principles of the present disclosure.

FIG. 3 illustrates various examples of the markers 114. The marker 114 may have a ring, ribbon shape configured to wrap around the distal portion 144 of the ophthalmic surgical tool 130. The marker 114 may have an inner surface 116 and an outer surface 118. The inner surface 116 may have adhesives and be configured to adhere or bond to an exterior surface of the ophthalmic surgical tool 130. The exterior surface of the distal portion 144 of the ophthalmic surgical tool 130 may have a circumferential groove configured to accommodate the ring, ribbon shape marker 114. Thus, the marker 114 may fit securely in the circumferential groove. The outer surface 118 of the marker 114 may have colors or patterns configured to distinguish the marker 114 from other elements in the fundus image.

One or more markers 114 may be used for the ophthalmic surgical tool 130. The marker 114 may be formed of bio-compatible and/or synthetic materials, such as sterile plastic. In some embodiments, the marker 114 may be a layer of paint inscribed on an exterior surface of the distal portion 144 of the ophthalmic surgical tool 130. The markers 114 may overlap each other or be separated from each other. The markers 114 may have one or more high contrast colors. For example, the markers 114 may have a green color, which does not appear in a typical fundus image. Thus, the green markers 114 may be distinguished from other elements in the fundus image.

The markers 114 may have various color, texture, or spectral contrast. In particular, the markers 114 may include patterns that may identify an orientation and angle of the ophthalmic surgical tool 130. For example, as shown in FIG. 3, marker 114a may have a solid high-contrast color. When the ring, ribbon shape marker 114a is cut open, the marker 114a may be a ribbon in solid color. In another example, marker 114b may have a texture pattern that may distinguish the marker 114b from the background fundus image. Exemplary marker 114c may include an infrared color configured to reflect or emit infrared light. Markers 114 with various spectral absorption/emission also may be used.

The markers 114 may include letters, numbers, bar codes, pattern, symbols, or pictures. Exemplary marker 114d may include letters. As shown in FIG. 3, assuming that the marker 114d wraps 360 degrees around the distal portion 144 of the ophthalmic surgical tool 130, a letter "A" may be positioned near the zero degree position and the letter "E" may be positioned near the 360 degree position. Letters "B," "C," and "D" may be positioned in between "A" and "E" at respective positions.

Thus, based on the orientation of the letters, the rotational position of the marker 114d and indirectly the rotational position of the ophthalmic surgical tool 130 may be determined. Exemplary marker 114e may include numbers "1" to "5." Similarly, the numbers may indicate a rotational position of the ophthalmic surgical tool 130. Further, the orientation of the letters or number also may indicate a tilting angle of the ophthalmic surgical tool 130. For example, the numbers or letters may be orientated relatively to the distal tip 146 of the ophthalmic surgical tool 130 such that the bottoms of the numbers or letter face toward the distal tip 146. Thus, based on the orientation of the numbers or letters, the tilting angle of the distal tip 146 may be determined.

Exemplary marker 114f may include barcodes or stripes. The direction of the stripes may indicate a tilting angle of the ophthalmic surgical tool 130. Further, the number of stripes may vary to indicate a rotational position of the marker 114f and indirectly, the rotational position of the ophthalmic surgical tool 130. Marker 114g has various dot patterns. The number of dots may indicate the rotational position of the marker 114f and the alignment of the dots may indicate a tilting angle of the marker 114f. Other symbols also may be used on the markers 114. For example, various symbols, such as shapes or non-character symbols may be used at different rotational positions of the markers 114h and 114i to indicate rotational positions. In addition, a picture may be used to indicate rotational and tilt positions of the marker 114j. Other patterns or symbols that may indicate an orientation and position of the ophthalmic surgical tool 130 also may be used on the markers 114.

Figure 4:
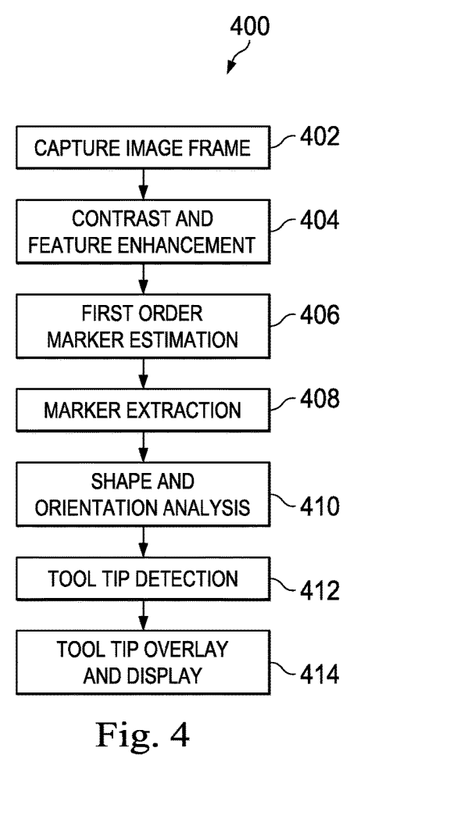
FIG. 4 is a flow chart illustrating a method for tool-tracking according to an aspect consistent with the principles of the present disclosure.

FIG. 4 is a flow chart illustrating a method 400 for tracking an ophthalmic surgical tool 130 inserted in an eye 101. As noted above, a light source 122 may introduce imaging light into the fundus of the eye 101. The reflected imaging light from the fundus may be guided by lenses 132 and 134 and received by imaging device 124. At 402, the imaging device 124 may capture images of the fundus. In particular, the imaging device 124 may capture frames of images to form a video. Each image frame may be forwarded to the image processor 126 to be processed and analyzed.

At 404, the image processor 126 may perform contrast and feature enhancement processing on the image frame. For example, the image processor 126 may receive the image frame in Red-Green-Blue (RGB) format. At 404, the image processor 126 may convert the RGB format image frame into a Hue-Saturation-Value (HSV) space. At 406, after the image frame has been enhanced to bring out the contrast and feature, the image processor 126 may determine a first-order estimation mask of the marker 114. For example, based on a predetermined color of the marker 114, the image processor 126 may apply criteria to the hue and saturation channels of the HSV image frame that may separate the marker 114 from the background in order to bring out and estimate the image of the marker 114.

At 408, the image processor 126 may extract the image of the marker 114 from the image frame. For example, the image processor 126 may implement a blob detection process to detect a boundary of the marker 114 in the image frame. A blob may be a region of the image frame where some properties, such as color and brightness, are approximately constant. The image processor 126 may search for regions of approximately constant properties in the image frame to detect blobs. Thus, the image processor 126 may find the boundary of the marker 114 and extract the marker 114 from the image frame.

At 410, the image processor 126 may analyze the shape and orientation of the marker 114 extracted from the image frame. Based on a predetermined pattern and color, the image processor 126 may determine the orientation of the marker 114 in the image frame. For example, if the marker 114 has stripes, the image processor 126 may determine the orientation of the marker 114 based on the orientation and direction of the stripes.

At 412, the image processor 126 may determine the position and orientation of the distal tip 146 of the ophthalmic surgical tool 130. In particular, based on the position and orientation of the marker 114, the image processor 126 may determine the position and orientation of the distal tip 146 of the ophthalmic surgical tool 130. For example, the marker 114 may be positioned from the distal tip 146 of the ophthalmic surgical tool 130 by a predetermined distance and may have a pattern that indicates a pointing direction of the ophthalmic surgical tool 130, e.g., a strip or an arrow. Thus, based on the position and the pattern of the marker 114, the image processor 126 may determine the position of the distal tip 146 of the ophthalmic surgical tool and the pointing direction or orientation of the ophthalmic surgical tool.

At 414, the image processor 126 may display and overlay indicators to indicate the distal tip 146 of the ophthalmic surgical tool 130 or other surgical data for surgical guidance. For example, the image processor 126 may generate an indicator, such as a box, a circle, a star, or an arrow, and overlay the indicator into the image frame at the position of the distal tip 146 of the ophthalmic surgical tool 130. Further, the indicator may indicate an orientation, e.g., a pointing angle, of the ophthalmic surgical tool 130. For example, an arrow may be used as the indicator to indicate the pointing direction of the ophthalmic surgical tool 130. Further, the indicator may also include an image, such as an OCT image of a region of the retina 112, or a surgical setting parameter, such as a cutting speed of a vitrectomy probe. The display 128 may display the image frame overlaid with the indicators.

Figure 5:
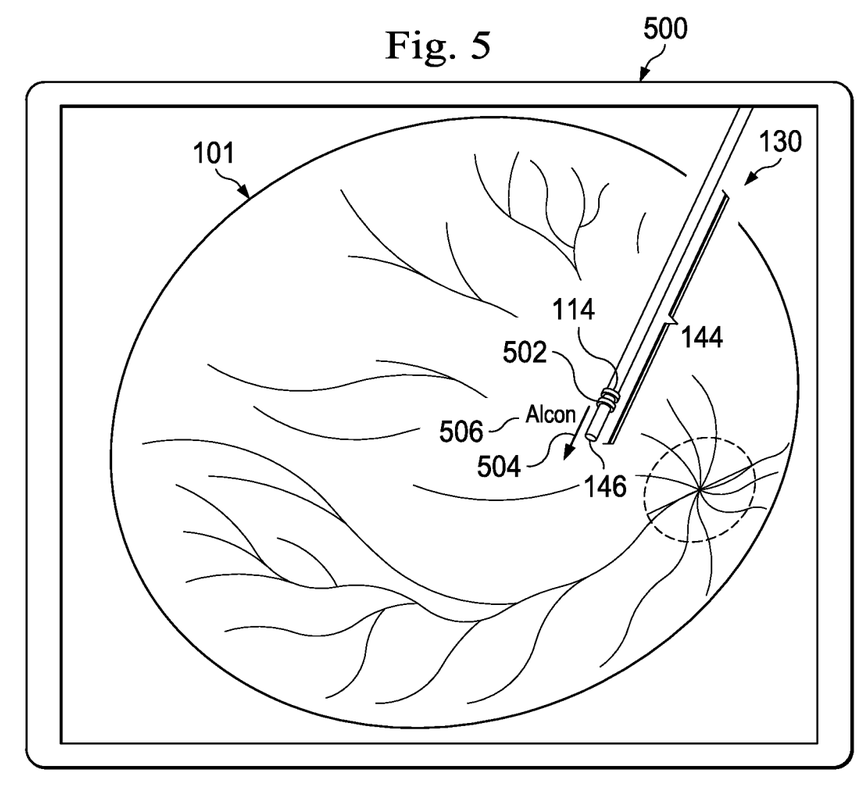
FIG. 5 illustrates an image of a fundus during an ophthalmic surgery according to an aspect consistent with the principles of the present disclosure.

FIG. 5 illustrates a fundus image 500 during an ophthalmic surgery. The fundus image 500 may be displayed or processed and displayed on the display 128. As shown in the fundus image 500, the distal portion 144 of the ophthalmic surgical tool 130 is inserted into the eye 101. The distal portion 144 may have a marker 114. After the image processor 126 extracts the marker image and determines the position and orientation of the marker 114, the image processor 126 may generate and overlay indicators 502, 504, and 506 into the fundus image.

Indicator 502 may be a dot positioned over the marker 114 or at a position of the surgical tool 130 in the fundus image 500. Thus, the indicator 502 may indicate the position of the marker 114 or the position of the surgical tool 130 in real time. Indicator 504 may be an arrow positioned on or adjacent to the marker 114. The arrow of indicator 504 may indicate an orientation or pointing position of the ophthalmic surgical tool 130. Indicator 506 may be text or image positioned at or adjacent to the marker 114. The indicator may include name or description of the ophthalmic surgical tool. The indicator also may include diagnosis information, surgical status, warnings, or other information. For example, the indicator may include the brand name, identification, and/or functional description. In the example shown in FIG. 5, indicator 506 has the text: "Alcon" to indicate the name brand of the ophthalmic surgical tool. In some embodiments, operating parameters, such as temperature, flow rate, revolutions per minute (RPM) speed, pressure, and the like, may be included in the indicator 506 to provide additional information to the user. In other embodiments, images of the tissue under examination from other imaging modalities, such as optical coherence tomography (OCT), fluorescein angiography (FA), and the like, may be included in the indicator 506 to provide additional guidance to the user.

The image processor 126 may perform the method 400 for each image frame as the image frame is displayed to continuously track the position and orientation of the distal tip 146 of the ophthalmic surgical tool 130 in real time. Thus, the display 128 may display the indicators 502, 504, and 506 in a real-time video of the fundus to track the position and movement of the distal tip 146 of the ophthalmic surgical tool 130. Accordingly, a surgeon may view the display 128 to visualize the movement of the ophthalmic surgical tool 130 in the eye 101 during a surgery.

The above systems and methods may be applied to track an infrared marker 114 using an imaging device 124 configured to capture images in infrared spectrum. Further, an OCT enabled surgical tool 130 may use the above systems and methods to track the area of the eye 101 being imaged by the OCT surgical probe 130 around the area of the distal tip 146 of the OCT surgical probe 130.

In some embodiments, the indicator may include identification or parameters of the ophthalmic surgical tool 130. For example, the indicator may identify that the ophthalmic surgical tool 130 is an irrigation tool with a certain liquid flow rate, pressure, and temperature. By displaying these parameters, a surgeon may keep track of the operation of the ophthalmic surgical tool 130 without looking away from the display 128.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. An ophthalmic surgical tool tracking system comprising:
   an ophthalmic surgical tool comprising a distal portion configured to be inserted into an eye;
   a marker positioned at the distal portion of the ophthalmic surgical tool, the marker including a pattern; and
   a tool position detection system comprising:
      a light source configured to introduce an imaging light into a fundus of the eye, the light source configured to be inserted into the eye;
      an imaging device configured to receive the imaging light reflected from the fundus and capture an image of the fundus along with the distal portion of the ophthalmic surgical tool inserted into the eye; and
      a processor configured to determine a position and an orientation of the marker in the captured image of the fundus based on the pattern, wherein an orientation of the pattern in the captured image indicates the orientation of the marker positioned at the distal portion of the ophthalmic surgical tool.

2. The ophthalmic surgical tool tracking system of claim 1, wherein the processor is configured to:
   process the captured image to identify the marker;
   generate an indicator indicating surgical data; and
   overlay the indicator to a display.

3. The ophthalmic surgical tool tracking system of claim 1, wherein the marker has one or more high-contrast features in a visible light range.

4. The ophthalmic surgical tool tracking system of claim 1, wherein the marker is a decal adhered to the ophthalmic surgical tool.

5. The ophthalmic surgical tool tracking system of claim 1, wherein the marker is inscribed on a surface or embedded into a wall of the ophthalmic surgical tool.

6. The ophthalmic surgical tool tracking system of claim 1, wherein the marker has a high-contrast feature in an infrared range or other spectral ranges.

7. The ophthalmic surgical tool tracking system of claim 2, wherein the processor is further configured to identify the marker in the captured image by:
   perform a contrast and feature enhancement process to the captured image;
   estimate an image of the marker in the enhanced image;
   extract the image of the marker from the enhanced image; and
   determine a shape, a position, and an orientation of the marker from the image of the marker.

8. The ophthalmic surgical tool tracking system of claim 2, wherein the surgical data includes one or more of a position of the ophthalmic surgical tool, an orientation of the ophthalmic surgical tool, an image, a surgical setting parameter.

9. The ophthalmic surgical tool tracking system of claim 2,
   wherein the imaging device is configured to capture a video of the eye, and
   wherein the processor is configured to continuously generate and overlay the indicator in real time.

10. An ophthalmic surgical tool comprising:
    a distal portion configured to be inserted into an eye; and
    a marker disposed at the distal portion and configured to be captured by an imaging device inserted into the eye, wherein the marker includes a pattern, as captured by the imaging device, that indicates an orientation and a position of a distal tip of the ophthalmic surgical tool.

11. The ophthalmic surgical tool of claim 10, wherein the marker has one or more high-contrast features in a visible light range.

12. The ophthalmic surgical tool of claim 10, wherein the marker is a decal attached to the ophthalmic surgical tool.

13. The ophthalmic surgical tool of claim 10, wherein the marker is inscribed on a surface or embedded into a wall of the ophthalmic surgical tool.

14. The ophthalmic surgical tool of claim 10, wherein the marker has a high-contrast feature in an infrared range or other spectral ranges.

15. A method for tracking an ophthalmic surgical tool inserted in an eye, the method comprising:
    inserting a light source into an eye, the light source configured to introduce an imaging light into a fundus of the eye;
    receiving, by an imaging device, the imaging light reflected from the fundus;
    capturing, by the imaging device, an image of the fundus along with a distal portion of an ophthalmic surgical tool inserted into the eye; and
    determining a position of a marker attached to the distal portion of the ophthalmic surgical tool, by processing the captured image to identify the marker, wherein the marker includes a pattern such that an orientation of the pattern in the captured image indicates an orientation of the marker.

16. The method of claim 15, wherein the determining a position of the marker comprises:
    generating an indicator indicating surgical data;
    overlaying the indicator on the captured image or a processed image; and
    displaying the captured image or the processed image with the overlaid indicator on a display.

17. The method of claim 15, wherein the processing the captured image comprises:
    performing a contrast and feature enhancement process to the captured image;
    estimating an image of the marker in the enhanced image;
    extracting the image of the marker from the enhanced image; and
    determining a shape, a position and an orientation of the marker from the image of the marker.

18. The method of claim 16, wherein the surgical data includes one or more of a position of the ophthalmic surgical tool, an orientation of the ophthalmic surgical tool, an image, a surgical setting parameter.

19. The method of claim 16, further comprising capturing a video of the eye and continuously generating and overlaying the indicator in real time.

20. The ophthalmic surgical tool tracking system of claim 1, wherein the light source is disposed on a second surgical tool different than the ophthalmic surgical tool.

* * * * *